US008703966B2

(12) United States Patent
DeBoef (10) Patent No.: US 8,703,966 B2
(45) Date of Patent: Apr. 22, 2014

(54) AEROBIC OXIDATIVE COUPLING FOR THE FORMATION OF BIARYLS

(75) Inventor: Brenton DeBoef, East Providence, RI (US)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 200 days.

(21) Appl. No.: 12/433,174

(22) Filed: Apr. 30, 2009

(65) Prior Publication Data

US 2009/0253921 A1     Oct. 8, 2009

Related U.S. Application Data

(63) Continuation of application No. PCT/US2007/085898, filed on Nov. 29, 2007.

(60) Provisional application No. 60/867,641, filed on Nov. 29, 2006.

(51) Int. Cl.
*C07D 209/04* (2006.01)
*C07D 307/91* (2006.01)

(52) U.S. Cl.
USPC .......................................... 548/466; 549/462

(58) Field of Classification Search
USPC .......................................... 548/466; 549/462
See application file for complete search history.

(56) References Cited

U.S. PATENT DOCUMENTS

| 5,756,604 | A | 5/1998 | Nakaoka et al. |
| 7,112,649 | B2 | 9/2006 | Liu et al. |
| 2005/0043541 | A1 | 2/2005 | Walter et al. |

OTHER PUBLICATIONS

Navarro et al., "A General Method for the Suzuki-Miyaura Cross-Coupling of Sterically Hindered Aryl Chlorides: Synthesis of Di- and Tri-ortho-subsituted Biaryls in 2-Propanol at Room Temperature", J. Am. Chem. Soc. 2003, No. 125, pp. 16194-16195.
Garcia-Cuadrado, D.; Braga, A. A. C.; Maseras, F.; Echavarren, A. M., Proton Abstraction Mechanism for the Palladium-Catalyzed Intramolecular Arylation. Journal of the American Chemical Society 2006, 128, 1066 (2 pages).
Campo, M. A.; Larock, R. C., Novel 1,4-Palladium Migration in Organopalladium Intermediates Derived from o-Iodobiaryls. Journal of the American Chemical Society 2002, 124, 14326 (2 pages).
Karig, G.; Moon, M.-T.; Thasana, N.; Gallagher, T., C-H Activation and Palladium Migration within Biaryls under Heck Reaction Conditions. Organic Letters 2002, 4, 3115 (4 pages).
Gonzalez, J. J. G., N.; Gomez-Lor, B.; Echavarren, A. M. , Synthesis of Spiro Polycyclic Aromatic Hydrocarbons by Intramolecular Palladium-Catalyzed Arylation Journal of Organic Chemistry 1997, 62 (6 pages).
LaFrance, M.; Rowley, C. N.; Woo, T. K.; Fagnou, K., Catalytic Intermolecular Direct Arylation of Perlluorobenzenes. Journal of the American Chemical Society 2006, 128, 8754 (3 pages).
Stahl, S. S., Palladium Oxidase Catalysis. Selective Oxidation of Organic Chemicals by Direct Dioxygen-Coupled Turnover. Angewandte Chemie, International Edition 2004, 43, 3400 (21 pages).
Kalyani, D.; Dick, A. R.; Anani, W. Q.; Sanford, M. S., A Simple Catalytic Method for the Regioselective Halogenation of Arenes. Organic Letters 2006, 8, 2523 (4 pages).
Hull, K. L.; Anani, W. Q.; Sanford, M. S., Palladium-Catalyzed Fluorination of Carbon-Hydrogen Bonds. Journal of the American Chemical Society 2006, 128, 7134 (2 pages).
Deprez, N. R.; Kalyani, D.; Krause, A.; Sanford, M. S., Room Temperature Palladium-Catalyzed 2-Arylation of Indoles. Journal of the American Chemical Society 2006, 128, 4972 (2 pages).
Dick, A. R.; Sanford, M. S., Transition Metal Catalyzed Oxidative Functionalization of Carbon-Hydrogen Bonds. Tetrahedron 2006, 62, 2439 (25 pages).
Desai, L. V.; Malik, H. A.; Sanford, M. S., Oxone as an Inexpensive, Safe, and Environmentally Benign Oxidant for C—H Bond Oxygenation. Organic Letters 2006, 8, 1141 (4 pages).
Kalyani, D.; Sanford, M. S., Regioselectivity in Palladium-Catalyzed C—H Activation/Oxygenation Reactions. Organic Letters 2005, 7, 4149 (4 pages).
Kalyani, D.; Deprez, N. R.; Desai, L. V.; Sanford, M. S., Oxidative C—H Activation/C—C Bond Forming Reactions: Synthetic Scope and Mechanistic Insights. Journal of the American Chemical Society 2005, 127, 7330 (2 pages).
Dick, A. R.; Hull, K. L.; Sanford, M. S., A Highly Selective Catalytic Method for the Oxidative Functionalization of C—H Bonds. Journal of the American Chemical Society 2004, 126, 2300 (2 pages).
Desai, L. V.; Hull, K. L.; Sanford, M. S., Palladium-Catalyzed Oxygenation of Unactivated sp3 C—H Bonds. Journal of the American Chemical Society 2004, 126, 9542 (2 pages).
Tsang, W. C. P.; Zheng, N.; Buchwald, S. L., Combined C—H Functionalization/C—N Bond Formation Route to Carbazoles. Journal of the American Chemical Society 2005, 127, 14560 (2 pages).
De Vries, J. G., A Unifying Mechanism for All High-Temperature Heck Reactions. The Role of Palladium Colloids and Anionic Species. Dalton Transactions 2006, 421 (9 pages).
Reetz, M. T.; Lohmer, G.; Schwickardi, R., A New Catalyst System for the Heck Reaction of Unreactive Aryl Halides. Angewandte Chemie, International Edition 1998, 37, 481 (3 pages).
Reetz, M. T.; Westermann, E.; Lohmer, R.; Lohmer, G., A Highly Active Phosphine-Free Catalyst System for Heck Reactions of Aryl Bromides. Tetrahedron Letters 1998, 39, 8449 (4 pages).
Toure, B. B.; Lane, B. S.; Sames, D., Catalytic C—H Arylation of SEM-Protected Azoles with Palladium Complexes of NHCs and Phosphines. Organic Letters 2006, 8, 1979 (4 pages).
Davidson, J. M.; Triggs, C., Reaction of Pallladium Complexes with Benzene and Toluene. Chemistry & Industry (London, United Kingdom) Mar. 12, 1966, p. 457 (1 page).
Van Helden, R.; Verberg, G., Oxidative Coupling of Aromatic Compounds with Palladium Salts. Recueil des Travaux Chimiques des Pays-Bas, 1965, 84, 1263 (11 pages).

(Continued)

*Primary Examiner* — Shawquia Young
(74) *Attorney, Agent, or Firm* — Gesmer Updegrove LLP (57) ABSTRACT

A method of catalytic oxidative coupling for the formation of hetero-coupled bis-arenes. The method includes placing a solvent, an arene compound, and a catalyst in a reactor having a oxidant atmosphere such that hetero-coupled bis-arenes are formed.

10 Claims, 3 Drawing Sheets

(56) References Cited

OTHER PUBLICATIONS

Itahara, T., Oxidation of 1-Benzoylpyrrole and 1-Aroylindoles by Palladium Acetate. Heterocycles 1986, 24, 2557 (7 pages).

Rouhi, A. M., Fine Chemicals. Chemical and Engineering News, Sep. 6, 2004, vol. 82, No. 36, pp. 49-58 (9 pages).

Li, Z., et al, Cu-catalyzed cross-dehydrogenative coupling: a versatile strategy for C—C bond formations via the oxidative activation of sp3 C—H bonds. Proceedings of the National Academy of Sciences of the United States of America, pp. 8928-8933 (2006). (6 pages).

Li, C.J. and Li, Z., Green chemistry: The development of cross-dehydrogenative coupling (CDC) for chemical synthesis. Pure and Applied Chemistry, vol. 78, No. 5, pp. 935-945 (2006). (11 pages).

Li, Z., et al., Studies on Cu-catalyzed asymmetric alkynylation of tetrahydroisoquinoline derivatives. Tetrahedron: Asymmetry, vol. 17, pp. 590-597 (2006). (8 pages).

Zhang, Y. and Li, C.J., Highly efficient cross-dehydrogenative-coupling between ethers and active methylene compounds. Angewandte Chemie, International Edition, 45, pp. 1949-1952 (2006). (4 pages).

Zhang, Y. and Li, C.J., DDQ-mediated direct cross-dehydrogenative-coupling (CDC) between benzyl ethers and simple ketones. Journal of the American Chemical Society, vol. 128, pp. 4242-4243 (2006). (2 pages).

Li, Z. and Li, C.J., Highly efficient CuBr-catalyzed cross-dehydrogenative coupling (CDC) between tetrahydroisoquinolines and activated methylene compounds. European Journal of Organic Chemistry, pp. 3173-3176 (2005). (4 pages).

Li, Z. and Li, C.J., CuBr-catalyzed direct indolation of tetrahydroisoquinolines via cross-dehydrogenative coupling between sp3 C—H and sp2 C—H bonds. Journal of the American Chemical Society, vol. 127, pp. 6968-6969 (2005). (2 pages).

Li, Z. and Li, C.J., Highly efficient copper-catalyzed nitro-mannich type reaction: Cross-dehydrogenative-coupling between sp3 C—H bond and sp3 C—H bond. Journal of the American Chemical Society, vol. 127, pp. 3672-3673 (2005). (2 pages).

Bundgaard, E. and Krebs, F. C., A comparison of the photovoltaic response of head-to-head and head-to-tail coupled poly{(benzo-2,1,3-thiadiazol-4,7-diyl)-(dihexyl[2,2']dithio-phene-5,5'-diyl)}. Polymer Bulletin (Heidelberg, Germany), vol. 55, pp. 157-164 (2005). (8 pages).

Crouch, D. J. et al., Thiophene and selenophene copolymers incorporating fluorinated phenylene units in the main chain: Synthesis, characterization, and application in organic field-effect transistors. Chemistry of Materials, vol. 17, pp. 6567-6578 (2005). (12 pages).

Campeau, L.C. and Fagnou, K., Palladium-catalyzed direct arylation of simple arenes in aynthesis of biaryl molecules. Chemical Communications (Cambridge, United Kingdom), pp. 1253-1264 (2006). (12 pages).

Joseph, J. K., et al., V2O5-O2 as a simple and efficient protocol for the oxidative coupling of 2-naphthols to binaphthois under mild reaction conditions. Catalysis Communications, vol. 7, pp. 184-186 (2006). (3 pages).

Ikeda, T., et al., Liquid-phase oxidative coupling of 2-naphthol by vanadium catalysts supported on MCM-41. Journal of Molecular Catalysis A: Chemical, pp. 235-240 (2005). (6 pages).

Habaue, S., et al., New asymmetric vanadium catalyst for highly selective oxidative coupling polymerization. Journal of Polymer Science, Part A: Polymer Chemistry, vol. 43, pp. 5872-5878 (2005). (7 pages).

Habaue, S., et al., Asymmetric oxidative coupling polymerization affording polynaphthylene with 1,1'-Bi-2-naphthol units. Journal of Polymer Science, Part A: Polymer Chemistry, vol. 42, pp. 4528-4534 (2004). (7 pages).

Habaue, S., et al., Copper(I)-catalyzed asymmetric oxidative coupling polymerization of 2,3-dihydroxynaphthalene using bisoxazoline ligands. Macromolecules, vol. 36, pp. 2604-2608 (2003). (5 pages).

Chen, X., et al., Cu(II)-catalyzed functionalizations of Aryl C—H bonds using O2 as an oxidant. Journal of the American Chemical Society, vol. 128, pp. 6790-6791 (2006). (2 pages).

Shiotani, A., et al., Selective coupling of dimethyl phthalate with palladium catalysts at atmospheric pressure. Journal of Molecular Catalysis, vol. 34, pp. 57-66 (1986). (10 pages).

Hatamoto, Y., et al., Oxidative cross-coupling of acrylates with vinyl carboxylates catalyzed by a Pd(OAc)2/HPMoV/O2 system. Organic Letters, vol. 6, No. 24, pp. 4623-4625 (2004). (3 pages).

Jia, C., et al., Highly efficient Pd-Catalyzed coupling of arenes with olefins in the presence of tert-butyl hydroperoxide as oxidant. Organic Letters, vol. 1, pp. 2097-2100 (1999). (4 pages).

Moritani, I. and Fujiwara, Y., Aromatic substitution of olefins by palladium salts. Department of Chemistry, Faculty of Engineering Science, Osaka University, Toyonaka, Osaka Japan. Synthesis , pp. 524-533 (1973). (10 pages).

Moritani, I. and Fujiwara, Y., Aromatic substitution of styrene-palladium chloride complex. Department of Chemistry, Faculty of Engineering Science, Osaka University, Toyonaka, Osaka Japan. Tetrahedron Letters No. 12, pp. 1119-1122 (1967). (4 pages).

Itahara, T., Oxidation of 1-benzoylpyrrole and 1-aroylindoles by palladium acetate. Heterocycles, vol. 24(9), pp. 2557-2562 (1986). (1 page).

Itahara, T., Oxidative coupling of quinones and aromatic compounds by palladium(II) acetate. Journal of Organic Chemistry, vol. 50, pp. 5546-5550 (1985). (5 pages).

Itahara, T., Arylation of aromatic heterocycles with arenes and palladium(II) acetate. Journal of Organic Chemistry, vol. 50, pp. 5272-5275 (1985). (4 pages).

Itahara, T., et al., Oxidative coupling of 1-(2,6-dichlorobenzoyl)pyrroles and pyrazoles and alkyl acrylates by palladium(II) acetate. Bulletin of the Chemical Society of Japan, vol. 57, pp. 3488-3493 (1984). (6 pages).

Garg, N. K., et al., Development of an enantiodivergent strategy for the total synthesis of (+)- and (−)-dragmacidin F from a single enantiomer of quinic Acid. Journal of the American Chemical Society, vol. 127, pp. 5970-5978 (2005). (9 pages).

Garg, N. K. and Stoltz, B. M., The formal total synthesis of dragmacidin B, trans-dragmacidin C, and cis- and trans-dihydrohamacanthins A. Tetrahedron Letters, vol. 46, pp. 2423-2426 (2005). (4 pages).

Garg, N. K., et al., The total synthesis of (+)-dragmacidin F. Journal of the American Chemical Society, vol. 126, pp. 9552-9553 (2004). (2 pages).

Garg, N. K., et al., The first total synthesis of dragmacidin D. Journal of the American Chemical Society, vol. 124, pp. 13179-13184 (2002). (6 pages).

Stahl, S. S., Palladium-catalyzed oxidation of organic chemicals with O2. Science, vol. 309, pp. 1824-1826 (2005). (4 pages).

Beck, E. M., et al., Mild aerobic oxidative palladium(II) catalyzed C—H bond functionalization: Regioselective and switchable C—H alkenylation and annulation of pyrroles. Journal of the American Chemical Society, vol. 128, pp. 2528-2529 (2006). (2 pages).

Grimster, N. P., et al., Palladium-catalyzed intermolecular alkenylation of indoles by solvent-controlled regioselective C—H functionalization. Angewandte Chemie, International Edition, vol. 44, pp. 3125-3129 (2005). (5 pages).

Yamada, T., et al., Oxidative coupling of benzenes with a,b-unsaturated aldehydes by the Pd(OAc)2/molybdovanadophosphoric acid/O2 system. Journal of Organic Chemistry, vol. 70, pp. 5471-5474 (2005). (4 pages).

Tani, M., et al., Pd(OAc)2-catalyzed oxidative coupling reaction of benzenes with olefins in the presence of molybdovanadophosphoric acid under atmospheric dioxygen and air. Journal of Organic Chemistry, vol. 69, pp. 1221-1226 (2004). (6 pages).

Yokota, T., et al., Direct coupling of benzene with olefin catalyzed by Pd(OAc)2 combined with heteropolyoxometalate under dioxygen. Journal of the American Chemical Society, vol. 125, pp. 1476-1477 (2003). (2 pages).

Yokota, T., et al., Aerobic oxidation of benzene to biphenyl using a Pd(II)/molybdovanadophosphoric acid catalytic system. Advanced Synthesis & Catalysis, vol. 344, pp. 849-854 (2002). (6 pages).

(56) References Cited

OTHER PUBLICATIONS

Okamoto, M., et al., Highly selective synthesis of biphenyl by the Pd(OAc)2/HPA/O2/Acoh catalyst system. Journal of Organometallic Chemistry, vol. 664, pp. 59-65 (2002). (7 pages).

Mukhopadhyay, S., et al., Air oxidation of benzene to biphenyl—a dual catalytic approach. Advanced Synthesis & Catalysis, vol. 343, No. 5, pp. 455-459 (2001). (5 pages).

Okamoto, M. and Yamaji, T., A selective synthesis of biphenyl by the Pd(OAc)2/MoO2(acac)2/O2/AcOH catalyst system. The Chemical Society of Japan, Chemistry Letters, pp. 212-213 (2001). (2 pages).

Lee, S. H., et al., Oxidative coupling of methyl benzoate with palladium/heteropolyacid catalysts. Journal of Molecular Catalysis A: Chemical, vol. 115, pp. 241-246 (1997). (6 pages).

Yatsimirskii, A. K., et al., Palladium(II)-catalyzed oxidative coupling of arenes by thallium(III). Tetrahedron, vol. 39, No. 14, pp. 2381-2392 (1983). (12 pages).

Davidson, J. M. and Triggs, C., Reaction of metal ion complexes with hydrocarbons. Part I. Palladation and some other new electrophilic substitution reactions. The preparation of palladium. Journal of the Chemical Society [Section] A: Inorganic, Physical, Theoretical, pp. 1324-1330 (1968). (7 pages).

Davidson, J. M. and Triggs, C., Reaction of Pd complexes with benzene and toluene. Chemistry & Industry (London, United Kingdom), pp. 457 (1966). (1 page).

Van Helden, R. and Verberg, G., Oxidative coupling of aromatic compounds with palladium salts. Recueil des Travaux Chimiques des Pays-Bas, vol. 84(9), pp. 1263-1273 (1965). (11 pages).

Shiotani, A., et al., Stereospecific dimerization of dimethyl phthalate with a phenanthroline-containing palladium catalyst. Journal of Molecular Catalysis, vol. 18, pp. 23-31 (1983). (9 pages).

Figure 1. Examples of Important Biaryl and Styrene Molecules

Figure 2. Examples of Substrates to be Oxidatively Coupled

Figure 3. Potential Products of Intramolecular Oxidative Coupling

Figure 4. Examples of Potential Catalysts

Figure 5. Examples of Potential Olefin Substrates and the Predicted Site of Arylation

AEROBIC OXIDATIVE COUPLING FOR THE FORMATION OF BIARYLS

CROSS REFERENCE TO RELATED APPLICATION

This present application is a continuation of International Patent Application No. PCT/US2007/085898, filed on Nov. 29, 2007, which claims priority to U.S. Provisional Patent Application Ser. No. 60/867,641 filed in the United States Patent and Trademark Office on Nov. 29, 2006, all of which are incorporated herein in their entirety.

BACKGROUND OF THE INVENTION

Figure 1:
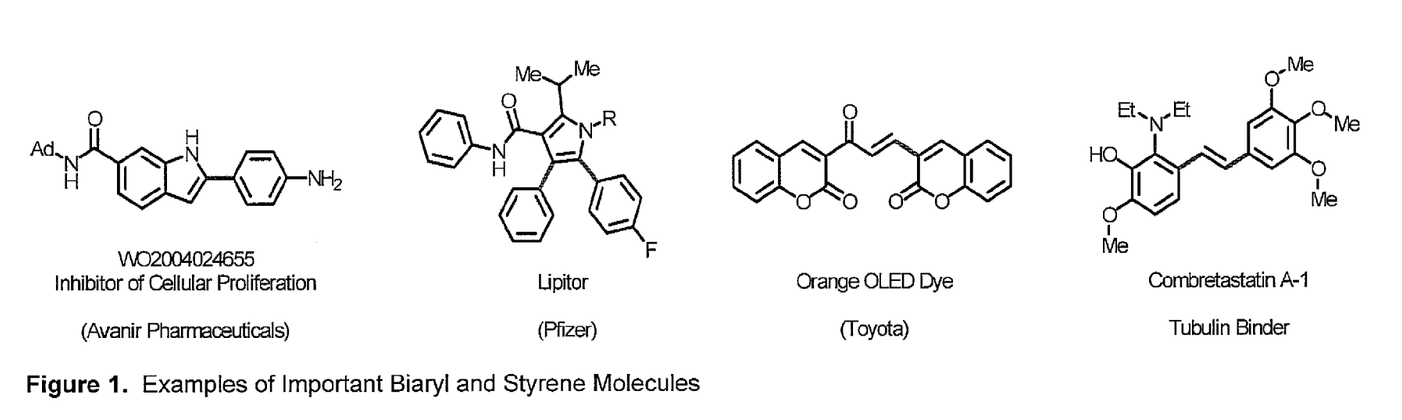
FIG. 1 illustrates examples of important biaryl and styrene molecules.

Bisarenes such as biaryls and styrenes are common components of many high value molecules such as pharmaceuticals, asymmetric conducting polymers, ligands and dyes for organic light emitting diodes as shown in FIG. 1. Two of the methods of choice, both in industry and academia, for the synthesis of these compounds are the Suzuki and Heck reactions, respectively. These reactions often work well; however, the overall process required to form an aryl-aryl or aryl-olefin bond is inherently inefficient, and it is far from ideal. Common coupling reactions, such as the Suzuki reaction, require that each of the substrates be pre-functionalized with groups such as boronic acids and bromides before the coupling reaction can occur. This adds extra steps to the overall synthesis of target molecules like those shown in FIG. 1. The current practice of installing these functional groups and then discarding them after the coupling reaction is inefficient and results in the production of large amounts of chemical waste. The generation and disposal of this waste has large economic and environmental impacts.

Carbon-hydrogen (C—H) bonds are ubiquitous in organic molecules, and, as a general rule, these C—H bonds are unreactive. That is why the Suzuki reaction requires the presence of boronic acids and bromides. However, for the reasons previously stated, the ideal synthetic process would not use these functional groups, it would simply couple the carbons of two C—H bonds to form a new C—C bond. Oxidative couplings of this type are rare and, as such, represent an underdeveloped, but potentially valuable, area of organic chemistry (Scheme 1).

Recently, numerous oxidative couplings (often called cross-dehydrogenative couplings) have been performed via the in situ formation of iminium ions. These intermediates are often formed via oxidation of the weak $sp^3$-hybridized C—H bonds of N,N-disubstituted benzylamines, such as N-phenyl tetrahydroisoquinolin, followed by the attack of a nucleophile. Notable recent work in this field has been performed by Li using nucleophiles such as indole, malononitrile, and nitromethane. Additionally, Li has recently described a method for oxidatively coupling allylic C—H bonds with malonate nucleophiles using a combination of cobalt and copper catalysts. In each of these examples, the terminal oxidant is tert-butyl hydroperoxide.

Radical mechanisms have also been employed in the oxidative formation of C—C biaryl bonds. Often these processes use stoichiometric amounts of radical initiators such as $FeCl_3$, and are used to synthesize polymers such as polythiophenes. This work has even been adapted to form chiral binapthalenes using asymmetric vanadium or copper catalysts and aerobic conditions. Recently, Yu has described a copper catalyzed reaction that oxidatively forms C—C, C—N, C—O, C—S, C—Cl, and C—Br bonds. Though extensive mechanistic studies of this process have not been performed, a radical pathway has been proposed.

Early work in the field of oxidative coupling used stoichiometric amounts of Pd(II) salts. These palladium complexes oxidatively couple by effectively deprotonating two aryl C—H moieties to form [Ar—Pd—Al] intermediates. Subsequently, the C—C bond is formed by reductive elimination. Alternatively, a Heck-type mechanism can be followed after one C—H deprotonation to form a styrene-type bond. Fujiwara performed noteworthy examples of this for the formation of styrenes. Additionally, Itahara used stoichiometric Pd(II) salts to couple electron-rich heteroarenes like furan with benzene, albeit in poor yields. Recently, Stolz used a stoichiometric amount of Pd(II) to perform the key oxidative coupling in his synthesis of dragmacidin. As with the Wacker oxidation, it was soon discovered that molecular oxygen could be used as the terminal oxidant when copper or silver cocatalysts were added: A notable example of this is the work of Gaunt, which demonstrated a Pd(II)—Cu(II)—$O_2$ method Scheme 1. Oxidative Coupling as an Efficient Method for Synthesizing Biaryls and Styrenes The oxidative couplings that have been previously reported can be divided into four categories based on their mechanisms: ionic, radical, organometallic deprotonation, and C—H activation. In each case, a stoichiometric oxidant is required for catalyst turnover. Examples of common oxidants are peroxides, olefins, and molecular oxygen ($O_2$).

for regioselectively alkenylating either the 2- or 3-position of indole. Recently, Ishii has discovered that phosphomolybdovanadic acids (HPMVs) are effective co-catalysts allowing for hundreds of catalytic turnovers. However, this HPMV-Pd (II) system has only been applied to the synthesis of biphenyl and cinnamates.

Arene-arene coupling using aerobic conditions is also a known process. However, it has only been used to synthesize dimeric products like biphenyl. Ishii has also used this system to couple olefins to each other. Interestingly, when equal amounts of electron-poor and electron-rich olefins were subjected to the oxidative conditions, very little dimerization was observed. Rather, the cross-products were favored. While Ishii does not explain this unique observation, it corroborates the interesting preliminary results that have been observed in our laboratory.

In addition to the palladium-catalyzed oxidative couplings that have been described herein, it should be noted that several research groups are currently pursuing the formation of C—C bonds via palladium catalyzed C—H/C-halogen couplings. While these processes are not formally oxidative, they provide insights into the mechanism of oxidative coupling. The majority of work in this field has utilized electron-rich arenes, as they are readily metallated by electrophilic Pd(II) catalysts. However, Maseras and Echavarren have used an intramolecular competition experiment to show that an electron-poor pyridine ring was selectively palladated in the presence of a phenyl ring (selectivity=2.1:1). Larock, Echavarren, and Gallagher have observed selectivity for the substitution of electron-poor arenes in Pd-migrations and couplings within biaryl moieties. Fagnou has exploited this phenomenon by developing a coupling reaction between pentafluorobenzene and bromobenzene. Maseras and Echavarren as well as Fagnou used computational modeling to provide insight into their observations. In both cases, it was concluded that the key C—H functionalization step did not proceed via palladium-mediated electrophilic aromatic substitution. Rather it involved the direct deprotonation of the arene's C—H bond following coordination of the arene to an electrophilic palladium intermediate. These experiments have produced a new paradigm through which aromatic palladations may be viewed.

In addition to the palladium-catalyzed oxidative couplings that form C—C bonds, aerobic oxidative coupling reactions have been developed to form C—N and C—O bonds. Most of these reactions involve the nucleophilic attack of an amide or alcohol nucleophile on an olefin that has been activated by coordination to a Pd(II) catalyst. While this mechanism is significantly different from those of the oxidative couplings proposed herein, these reactions involve the aerobic regeneration of catalytic Pd(II) species from Pd(O) intermediates. Work in this field has demonstrated that this oxidation process is significantly enhanced by the presence of carboxylic acids and/or coordinating solvents such as pyridine or DMSO.

A few examples of C—N and C—O formation do not involve electrophilic olefin-Pd(II) complexes. Notably, Sanford has shown that arenes and even alkanes can be oxidized to C—O, C—Cl, C—Br, and even C—C species using strong oxidants such as $PhI(OAc)_2$. She has rigorously shown that these reactions proceed though Pd(II)/Pd(IV) mechanisms. Recently, Buchwald showed that $Pd(OAc)_2/Cu(OAc)_2$ catalyzed the aerobic formation of carbazoles from 2-amino biphenyls. This reaction presumably proceeds via a mechanism that is similar to our preliminary results.

While significant advances in the field of oxidative coupling have been observed, the method as a whole is still rarely used for organic synthesis. A survey of the current chemical literature quickly reveals that the method of choice for the synthesis of bis-arenes and styrenes is still the Suzuki reaction—although C—H/C-halide coupling reactions are becoming increasingly important. The reasons for the lack of oxidative couplings are likely their limited substrate scope and their relatively high catalyst loadings

SUMMARY OF THE INVENTION

A novel chemical process whereby two carbon-hydrogen bonds within two aromatic molecules are formally broken; resulting in the formation of a new carbon-carbon bond that connects the two arenas. The catalyst for the reaction consists of a palladium salt and may or may not have ligands such as triphenylphosphine or bipyridine. Enhanced reactivity is observed in the presence of a co-catalyst such as copper (II) acetate, silver acetate, phosphomolybdovanadic acids. A carboxylic acid, or its salt, must be present in the reaction. Examples of this are acetic acid, benzoic acid, lithium acetate, and lithium carbonate. Finally, the terminal oxidant for the process is molecular oxygen or air. One atmosphere of either of these gasses is sufficient. However, greater pressures allow for increased reactivity.

The process of catalytic aerobic oxidative coupling for the formation of hetero-coupled bis-arenes is unprecedented.

This process provides a method by which the pharmaceutical and chemical industries can manufacture high-value molecules such as drugs and dyes in a cost effective and environmentally benign way. The method is cost effective and the substrates for the reaction are inexpensive. The process is environmentally benign-less amounts of toxic waste. By reducing the amount of the catalyst in the reactions will further reduce the input costs associated with the reaction. It will also allow for easier purification after the reaction is complete.

These and other features and objectives of the present invention will now be described in greater detail with reference to the accompanying drawings, wherein:

DESCRIPTION OF THE INVENTION

Palladium catalysts can selectively couple two different aromatic molecules via an process that uses $O_2$ as a terminal oxidant. Continued efforts in this field promise to provide new methods for the synthesis of small molecules and materials as well as insight into the chemical principles that govern oxidative coupling reactions.

The development of oxidative coupling reactions for the synthesis of both biaryl and styrene molecules, as well as the development of asymmetric oxidative coupling reactions. These reactions involve the formal "activation" and cross-coupling of two strong, non-acidic carbon-hydrogen (C—H) bonds to form a carbon-carbon (C—C) bond. Such processes are rare, however it has recently been discovered that oxidative coupling is a viable method for synthesizing biaryls and styrenes. This would expedite the synthesis of high value target molecules by eliminating the pre-functionalization steps that are commonly employed in modern synthetic chemistry-thus allowing them to be synthesized directly from plentiful and inexpensive feedstock chemicals. In addition to the basic science, the proposed technology should have environmental and economic benefits for the chemical and pharmaceutical industries.

Aerobic Oxidative Coupling as a Method for Biaryl Synthesis

The C—H bonds of arenes can be cross-coupled to form biaryl C—C bonds. Three key issues are the development of ligated palladium complexes that serve as stable catalysts for the oxidative coupling reaction, the elucidation of the reaction's mechanism, and the exploration of the reaction's substrate scope and limitations. These efforts should result in increased yields and lower catalyst loadings.

Aerobic Oxidative Coupling as a Method for Biaryl Synthesis

In surveying the chemical literature pertaining to the field of oxidative coupling, it was discovered that catalytic conditions, much less aerobic conditions, had not been applied to the synthesis of non-dimeric biaryl molecules. Presumably, previous researchers in this field assumed that these reactions would be plagued by homo-couplings. However, the opposite scenario has been demonstrated specifically that hetero-coupled biaryls are readily synthesized by oxidative coupling processes and the formation of dimeric biaryls is readily controlled by the reaction's solvent as shown in Table 1.

By using stoichiometric amounts of palladium salts (Entry 1) it was demonstrated that oxidative hetero-coupling was possible. Interestingly, switching the solvent from pure benzene to a 2:1 mixture of benzene and acetic acid inverted the selectivity of the reaction to favor the 2-pheny product 1 (Entry 2). It was quickly discovered that palladium acetate was the only suitable catalyst precursor [stoichiometric reactions with $PdCl_2$, $Pd(acac)_2$, and $Pd(TFA)_2$ failed to produce any arylation products].

Switching the substrate to benzofuran, lowering the catalyst loading to 25 mol %, and adding excessive amounts of the oxidant $Cu(OAc)_2$ provided comparable results to the stoichiometric reaction (Entry 3). (N-methyl indole is also arylated using the conditions, albeit in slightly poorer yield.) Benzoquinone was completely ineffective as an oxidant, and stronger oxidants such as $PhI(OAc)_2$ and benzoylperoxide produced complex mixtures of oxidized products.

It was discovered that $O_2$ is an excellent terminal oxidant for the formation of hetero-coupled biaryls. Lowering the amount of $Cu(OAc)_2$ and adding 1 atm of $O_2$ increased the conversion of the substrate and consequently the yield of oxidatively coupled products. Replacing the copper salt with AgOAc caused markedly lower conversions.

TABLE 1

Discovery of Oxidative Coupling for the Formation of Hetero-Coupled Biaryls

| Entry | X | Pd(OAc)$_2$ | Oxidant | O$_2$ | Solvent[a] | Additive[c] | Yield[b] 1 | Yield[b] 2 | Yield[b] 3 | Yield[b] 4 | Yield[b] Ph-Ph |
|---|---|---|---|---|---|---|---|---|---|---|---|
| 1 | N—Me | 100 mol % | None | None | Benzene | None | 13% | 40% | — | 10% | 2% |
| 2 | N—Me | 100 mol % | None | None | AcOH | None | 35% | 8% | — | 14% | — |
| 3 | O | 25 mol % | 4 equiv. Cu(OAc)$_2$[c] | None | AcOH | None | 41% | 2% | — | — | — |
| 4 | O | 25 mol % | 1 equiv. Cu(OAc)$_2$[c] | 1 atm | AcOH | None | 55% | 13% | 16% | — | 4% |
| 5 | O | 25 mol % | 1 equiv. Cu(OAc)$_2$[c] | 1 atm | AcOH | MeCN[d] | 63% | 19% | 6% | — | — |
| 6 | O | 25 mol % | 25 mol % HPMV[e] | 1 atm | AcOH | None | 69% | 1% | — | — | — |
| 7 | O | 10 mol % | 10 mol % HPMV[e] | 1 atm | AcOH | None | 62% | — | — | — | — |
| 8 | N—Me | 25 mol % | 1 equiv. Cu(OAc)$_2$[c] | 1 atm | AcOH | DMSO | — | — | — | 74% | — |
| 9 | O | 25 mol % | 1 equiv. Cu(OAc)$_2$[c] | 1 atm | Pyridine | None | — | — | — | 82% | — |

[a]Typical procedures (0.2 mmol substrate) used 2 mL of benzene and 1 mL of an additional solvent.
[b]GC Yield
[c]Assuming a Cu(I)/Cu(II) cycle, a stoichiometric amount of Cu(OAc)$_2$ is 2 equiv.
[d]1:1 (v/v) mixture
[e]HPMV = H$_4$PMo$_{11}$VO$_{40}$ Assuming that the observed oxidative coupling proceeds via a Pd(0)/Pd(II) mechanism, the problematic step in these reactions appears to be the oxidation of Pd(0) species back to catalytically active Pd(II) moieties. The reactions are plagued by the formation of palladium "mirrors" on the sides of the reaction flasks. Increased catalyst loadings lead to higher yields but lower turnover numbers. These observations indicated that the formation of Pd(0) colloids might be responsible for the catalyst degradation. However, addition of colloid inhibitors such as tetraphenylphosphonium bromide and N,N-dimethylglycine completely extinguished the catalyst activity.

Catalytic amounts of a phosphomolybdovanadate (HPMV) oxidant proved to be the best method for the oxidative hetero-coupling, allowing for catalyst loadings of 10 mol % with minimal deterioration of the yield (Entry 7). Interestingly, these reactions did not form palladium mirrors, even with 25 mol % loadings.

Addition of coordinating solvents such as acetonitrile (MeCN), pyridine, and methyl sulfoxide (DMSO) also inhibited the formation of palladium "mirrors" on the reaction vessels. Additionally, acetonitrile increased the yield of the oxidative coupling when $Cu(OAc)_2$ was the oxidant (Entry 5). Similar yield enhancements were not observed in the presence of HMPV. The other coordinating solvents caused even more pronounced effects. Most notably, DMSO inverted the selectivity of the oxidative coupling (Entry 8). The sole product was the homo-coupled 2,2'-biindole. Addition of pyridine to the reaction quenched the catalysis. However, when acetic acid was removed from the reaction (benzene was still present in excess), the exclusive formation of dimeric products was observed (Entry 9).

Aerobic Oxidative Coupling as a Method for Biaryl Synthesis

Described herein the palladium catalyzed aerobic oxidative coupling of arenes are as follows: (1) the development of ligated palladium complexes that serve as stable catalysts, (2) the elucidation of the reaction's mechanism, and (3) the exploration of the reaction's substrate scope and limitations. Future work in this field will develop asymmetric oxidative couplings and apply these reactions to the total synthesis of complex molecules, and the synthesis of conjugated polymers.

Figure 2:
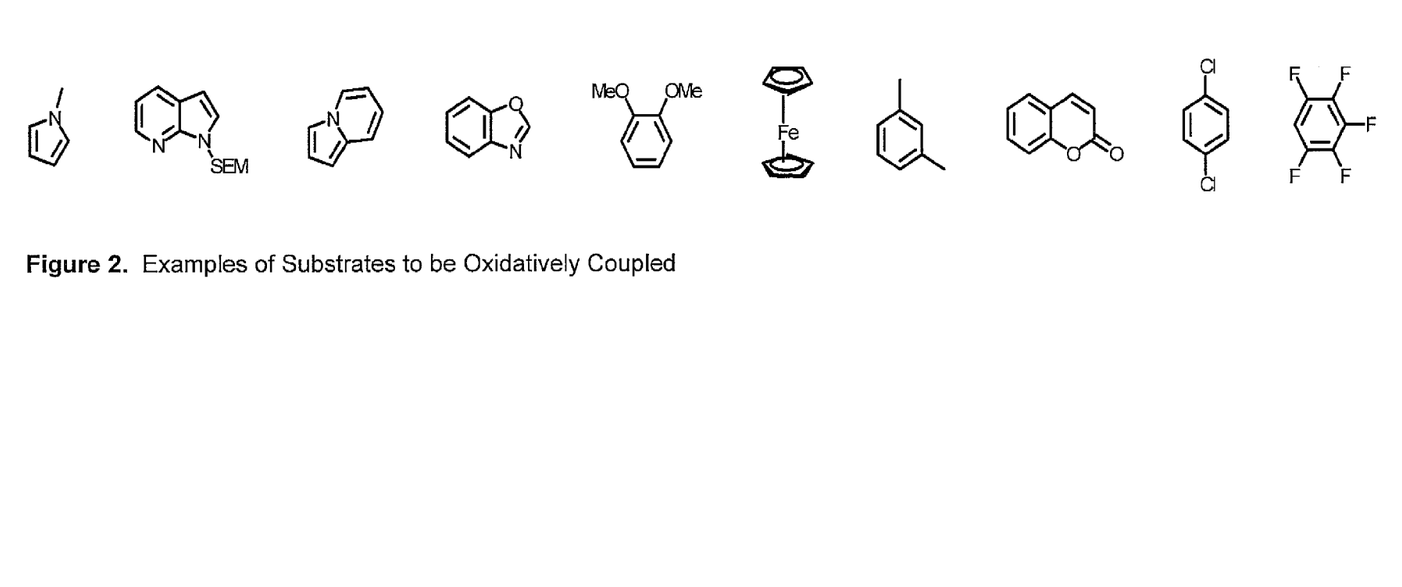
FIG. 2 illustrates examples of substrates to be oxidatively coupled.

A representative sample of the substrates that are to be oxidatively coupled is shown below (FIG. 2).

Figure 3:
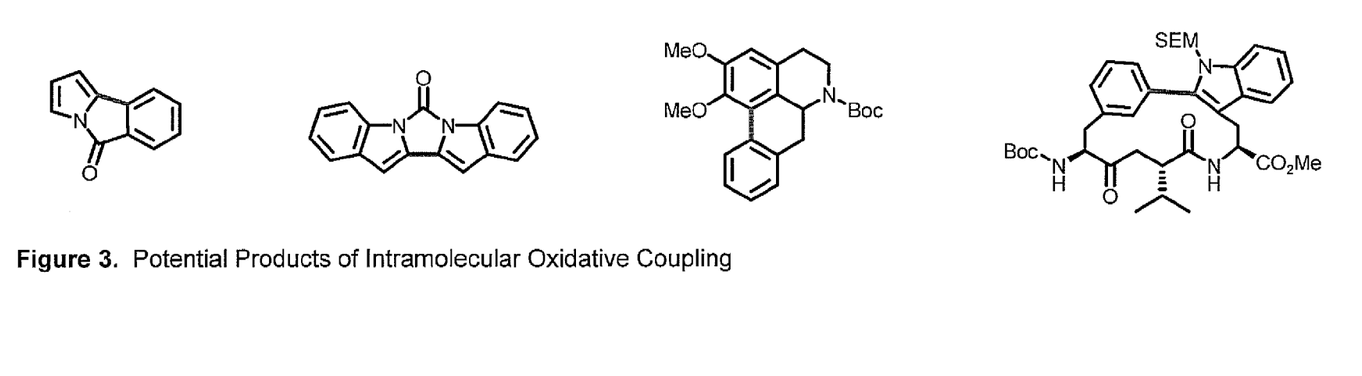
FIG. 3 illustrates potential products of intramolecular oxidative coupling.
Figure 4:
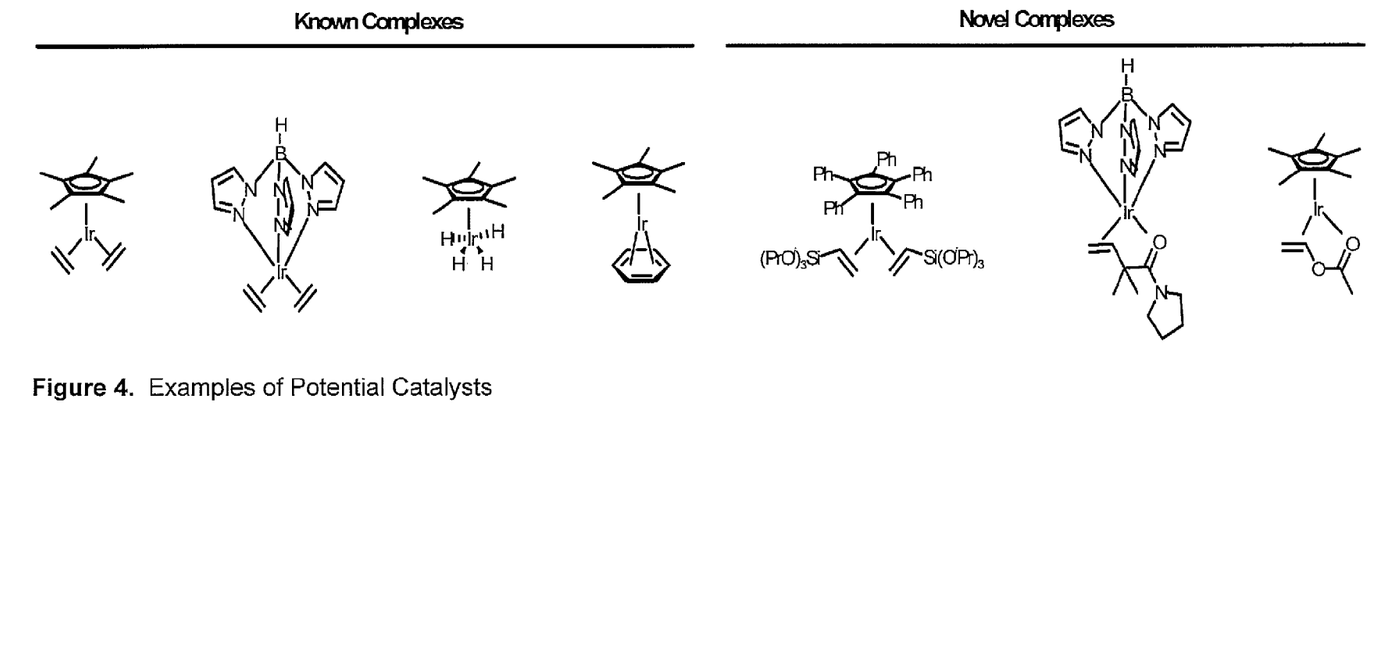
FIG. 4 illustrates examples potential catalysts.
Figure 5:
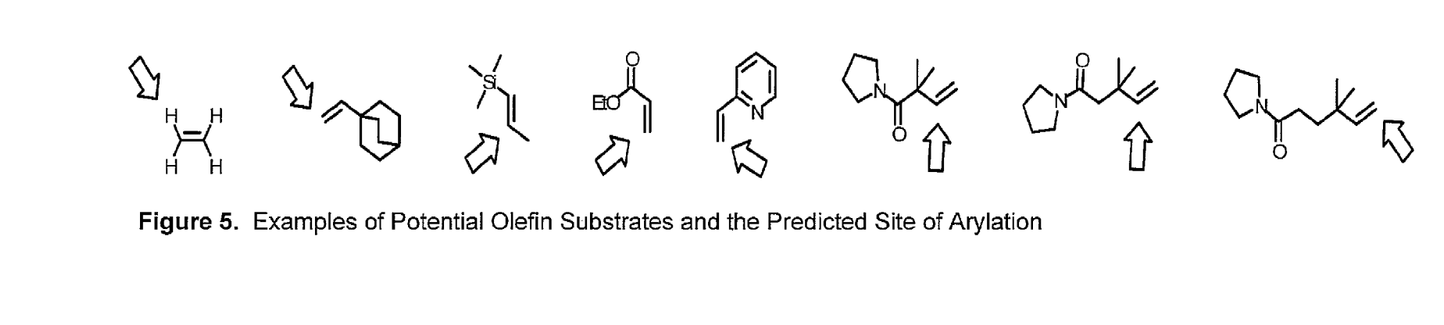
FIG. 5 illustrates examples of potential olefin substrates and the predicted site of arylation.

In addition, substrates that can undergo intramolecular coupling are shown in FIG. 3. Simple substrates such as N-benzoyl pyrroles are expected to proceed swimmingly in light of earlier work using stoichiometric $Pd(OAc)_2$. However, more complex substrates can also be utilized such as peptides that contain proximal tryptophan and phenyl alanine residues. These processes represent a simple method for synthesizing conformationally restricted peptides and peptidomimetics.

Development of Ligated Catalysts

One of the primary objectives of the palladium-catalyzed approach to oxidative coupling was the development of ligated catalysts that selectively produce homo-coupled products. The development of ligated catalysts allow for lower catalyst loadings due to diminished colloid formation and greater catalyst activity. It has been shown along with literature precedent that ligands play a critical role in the course of reactions that functionalize the C—H bonds of arenes. Fagnou's catalyst that arylated electron-poor arenes via proton abstraction contained an electron-donating phosphine ligand, $P^tBu_2Me$. In general, reactions that substitute electron-rich arenes have been accomplished using electron-donating ligands such as N-heterocyclic carbenes, as well. However, the arylation of SEM-protected indoles is best accomplished using acylated versions of these ligands.

The development of ligated catalysts has proceeded by a systematic investigation of amine, phosphine, and carbene ligands. This systematic study of both the hard/soft nature of the ligating atom as well as the electron-donating/withdrawing abilities of the ligand will be used to optimize the oxidative homo-coupling and hetero-coupling reactions.

The electronic nature of the arenes determines the selectivity of the reaction. Using our best reaction conditions, electron-rich arenes such as N-substituted indoles and benzofurans are selectively coupled to electron-neutral or poor arenes such as benzene and pentafluorobenzene. However, the addition of coordinating solvents (DMSO or pyridine) alters the selectivity of the reaction, so the more electron-rich arene preferentially homo-couples-even in the presence of excess benzene. As a general rule, substrates that contain Lewis basic lone pairs, such as benzothiophene or N-methylimidazole, or N—H bonds, such as pyrrole and uracil, fail to produce any coupled products.

The reaction proceeded via one of two possible mechanisms (Scheme 2). According to Mechanism A, the first step is the electrophilic metallation of the electron-rich arene at its most nucleophilic position (9). Such processes are well-known. Indole and benzofuran substrates then undergo a migration of palladium from the 3- to the 2-position (10). Following the formation of the [Ar—Pd—OAc] species 11, the electron-poor arene (e.g. benzene) is deprotonated via an intramolecular abstraction process that proceeds through a 6-membered cyclic transition state (12). Such mechanistic steps are rare, but Fagnou, Maseras, and Echavarren have recently studied them both experimentally and computationally. Following this unique step, reductive elimination of the diaryl palladium intermediate affords the product and Pd(0) which is oxidized back to Pd(II) using an organometallic oxidant such as $Cu(OAc)_2$ or HPMV.

Scheme 2. Two Possible Mechanisms for the Aerobic Oxidative Coupling of Arenes

L = CH₃CN, for Pd(0)/Pd(II) mechanisms or OAc for Pd(II)/Pd(IV) mechanisms

Alternatively, the two key steps in the proposed mechanism, electrophilic substitution and proton abstraction, could occur in reverse order (Scheme 2, Mechanism B).

Both Mechanisms A and B assume that the intermediates are palladium complexes that exist in the 0 or +2 oxidation states. Most palladium-mediated oxidative processes are assumed to proceed through such mechanisms. However, Sanford has recently demonstrated that strong oxidants such as PhI(OAc)$_2$ produce palladium intermediates in the +4 oxidation state. Keeping this possibility in mind as well as the mechanistic possibilities A and B, the following section of this proposal presents a method for distinguishing between all of these possible mechanisms.

The electrophilic substitution step that forms either intermediate 9 or 16 should prefer more electron-rich substrates. Consequently, if equimolar amounts of 6-methoxybenzofuran and benzofuran were to be subjected to the reaction conditions, both Mechanisms A and B predict that the major product would result from the oxidative coupling of 6-methoxybenzofuran (Scheme 3). Analogously, the intramolecular proton abstraction that proceeds through transition states similar to 12 or 14 should prefer the more acidic protons of electron-poor arenes. A competition experiment between equimolar amounts of benzene and pentafluorobenzene produces greater amounts of the fluorinated product (Scheme 3).

Scheme 3. Proposed Competition Experiments

Validation of Electrophillic Substitution

[Reaction should be stopped prior to complete converion of either substrate]

Weakly coordinating solvents, such as acetonitrile, probably occupy the open coordination sites on the palladium intermediates. Possible solvent coordination has been shown in Scheme 2, but the exact number of coordinated solvents, the mode of acetate binding, and the cis/trans stereochemistry of the intermediates is unknown. It has been indicated that pyridine or DMSO, solvents with greater coordinating ability, cause the formation of bis-indole and bis-benzofuran products. Apparently, the coordination of these solvents prevents the intramolecular proton abstraction mechanism. These ligands must coordinate tightly to the metal, and can only be replaced by highly nucleophilic arenes. Thus, only homo-coupled products of the electron-rich arenes are observed.

The key mechanistic principle to be addressed is the origin of the hetero-coupled product. Specifically, why does Pd(OAc)$_2$ prefer to interact with electron-rich arenes, while 11, another Pd(II) complex, prefers to interact with electron-poor arenes? (This question assumes Mechanism A. The inverse question should be asked, if the reaction is shown to proceed via Mechanism B).

In order to test the hypothesis about the solvent effects and to distinguish between Mechanisms A and B, complexes containing [Ar—Pd—OAc] similar to 11 and 15 will be synthesized by oxidative addition of the corresponding bromo- or iodoarenes to Pd(0) and subsequent metathesis with AgOAc. (The bromide corresponding to 19 is a known compound.) These procedures will be carried out in acetonitrile, pyridine, and DMSO or in the presence of a suitable ligand (see previous section). If stable, the consequent palladium complexes (such as 18 and 19) will be isolated and characterized.

These complexes will then be reacted with both electron-rich and poor arenes in order to ascertain whether they are feasible intermediates in the reaction pathway (Scheme 4). Comparison of the rates of these reactions with those of the stoichiometric oxidative coupling will also reveal if either step is rate-determining [in the absence of Pd(0) oxidation].

Additionally, these reactions will be performed in the presence of a stoichiometric amount of an oxidant such as Cu(OAc)$_2$ or HMPV. Rate enhancements in the presence of the oxidant will provide significant evidence for the presence of Pd(IV) intermediates. While similar rates with and without oxidant will be indicative of a Pd(0)/Pd(II) mechanism.

The insight gained from these experiments should allow for discrimination between mechanisms A and B. Additionally, these stoichiometric experiments will answer the central question posed by our preliminary results: Why do some Pd(II) complexes prefer to undergo proton abstraction mechanisms while others prefer to undergo electrophilic substitution processes? We hypothesize that the number of acetates and possibly their coordination mode ($\eta^1$ vs. $^3$) may be the key to answering this question. Assuming Mechanism A, the Pd(OAc)$_2$ [two acentates, both $\eta^3$ in weakly coordinating solvent] may prefer to be attacked by a nucleophilic arene, dissociating an acetate. The consequent intermediate 15, would be ligated by one or two solvent molecules (depending on the coordination mode of the acetate). This intermediate would most likely react with any nearby arene, particularly if the solvent were a weak ligand. If the solvent were a strong ligand (e.g. pyridine), it may only react with a nucleophilic arene. Otherwise, the interaction with the electron-poor arene would be favored (because it is in excess), and this interaction would involve proton abstraction rather than electrophilic substitution, because the electron-poor arene is an inferior nucleophile. As previously mentioned, this is only our working hypothesis, the experiments herein will corroborate or refute it.

Further refinement of palladium-catalyzed aerobic oxidative coupling reactions and their application to chemical synthesis will be addressed. This will most likely include the development of catalytic asymmetric coupling reactions, the total synthesis of natural products, and the use of oxidative couplings as a method for polymerizing arenes.

Oxidative Coupling

The palladium-catalyzed aerobic hetero-coupling of arenes described is suitable for common conditions, as its reagents are stable to moisture and air. The only problematic aspect is the long reaction time (approx. 3 hrs.). This is alleviated using higher temperatures or microwaves.

Although the present invention has been shown and described with respect to several preferred embodiments thereof, various changes, omissions and additions to the form and detail thereof, may be made therein, without departing from the spirit and scope of the invention.

What is claimed is:

1. A method of catalytic oxidative coupling for the formation of hetero-coupled biaryls, said method comprises:
    a. providing a reactor such that said reactor maintains an oxidant atmosphere;
    b. providing a solvent;
    c. providing an arene, wherein the arene is and wherein X is selected from N-methyl and oxygen;
    d. providing a catalyst;
    e. combining the arene, catalyst and solvent in the reactor such that hetero-coupled biaryls are formed.

2. The method of claim 1, wherein the catalyst is palladium salt which may or may not includes a ligand such as triphenylphoshine or bipyridine.

3. The method of claim 1, wherein the method further comprises providing a co-catalyst selected from the group consisting of copper (II) acetate, silver acetate or phosphomolybdovanadic acids.

4. The method of claim 1, wherein the method further comprises providing a carboxylic acid or salt selected from a group consisting of acetic acid, benzoic acid, lithium acetate or lithium carbonate.

5. The method of claim 1, wherein the solvent may be selected from benzene, pyridine, dioxane, arene, or mixtures thereof.

6. The method of claim 1, wherein the oxidant may be selected from a group consisting of oxygen, peroxide, copper acetate or silver acetate.

7. The method of claim 1, wherein the oxidant atmosphere is at least 1 atmosphere of oxygen.

8. The method of claim 1, wherein the method further comprises providing an additive selected from a group consisting of acetonitrile, pyridine, and methyl sulfoxide.

9. The method of claim 1, wherein X in is selected from N-methyl.

10. The method of claim 1, wherein X in is selected from oxygen.

* * * * *

UNITED STATES PATENT AND TRADEMARK OFFICE
CERTIFICATE OF CORRECTION

PATENT NO.      : 8,703,966 B2  
APPLICATION NO. : 12/433174  
DATED           : April 22, 2014  
INVENTOR(S)     : Brenton DeBoef

It is certified that error appears in the above-identified patent and that said Letters Patent is hereby corrected as shown below:

In the Specification

In Column 3, line 50 of the issued Patent, please delete "though" and replace with --through--

In Column 7, line 21 of the issued Patent, please delete "acetonitrile" and replace with --acetontrile--

Signed and Sealed this  
Fifteenth Day of July, 2014

Michelle K. Lee  
*Deputy Director of the United States Patent and Trademark Office*